US010912678B2

(12) United States Patent
Andersen et al.

(10) Patent No.: US 10,912,678 B2
(45) Date of Patent: Feb. 9, 2021

(54) MULTIPLE SPOT PHOTOMEDICAL TREATMENT USING A LASER INDIRECT OPHTHALMOSCOPE

(71) Applicant: Topcon Medical Laser Systems, Inc., Santa Clara, CA (US)

(72) Inventors: Dan E. Andersen, Menlo Park, CA (US); David H. Mordaunt, Los Gatos, CA (US)

(73) Assignee: TOPCON MEDICAL LASER SYSTEMS INC., Santa Clara, CA (US)

( * ) Notice: Subject to any disclaimer, the term of this patent is extended or adjusted under 35 U.S.C. 154(b) by 105 days.

(21) Appl. No.: 16/238,460

(22) Filed: Jan. 2, 2019

(65) Prior Publication Data

US 2019/0167472 A1  Jun. 6, 2019

Related U.S. Application Data

(62) Division of application No. 11/595,423, filed on Nov. 8, 2006, now abandoned.
(Continued)

(51) Int. Cl.
*A61F 9/008* (2006.01)
*A61B 3/00* (2006.01)
(Continued)

(52) U.S. Cl.
CPC ............ *A61F 9/008* (2013.01); *A61B 3/0008* (2013.01); *A61B 3/12* (2013.01); *A61F 9/00821* (2013.01);
(Continued)

(58) Field of Classification Search
CPC ................................ A61F 9/008; A61B 18/20
(Continued)

(56) References Cited

U.S. PATENT DOCUMENTS

| | | |
|---|---|---|
| 5,391,165 A | 2/1995 | Fountain et al. |
| 5,423,798 A | 6/1995 | Crow |

(Continued)

FOREIGN PATENT DOCUMENTS

| | | |
|---|---|---|
| EP | 0721129 A1 | 7/1996 |
| JP | 2000/500043 A | 1/2000 |

(Continued)

OTHER PUBLICATIONS

International Written Opinion received for PCT Patent Application No. PCT/US2006/044296, dated Aug. 3, 2007, 5 pages.
(Continued)

*Primary Examiner* — Lynsey C Eiseman
(74) *Attorney, Agent, or Firm* — Dentons US LLP

(57) ABSTRACT

A laser indirect ophthalmoscope (LIO) apparatus for photomedical treatment and/or diagnosis is presented. The LIO apparatus allows multiple spot ophthalmic surgery to be performed in a wider range of patient positions and less intrusively than currently available methods. The LIO apparatus utilizes a separate or integral beam multiplier that generates one or more optical beams via spatial and/or temporal separation, and an optical system that conditions and directs the one or more optical beams to a target to form a pattern. The LIO apparatus includes a headset, and is therefore wearable by the user (e.g., a physician).

13 Claims, 14 Drawing Sheets

Related U.S. Application Data

(60) Provisional application No. 60/737,548, filed on Nov. 16, 2005.

(51) Int. Cl.
| | |
|---|---|
| *A61B 3/12* | (2006.01) |
| *A61B 90/50* | (2016.01) |
| *A61B 18/00* | (2006.01) |
| *A61B 18/20* | (2006.01) |
| *A61B 18/22* | (2006.01) |
| *A61N 5/06* | (2006.01) |

(52) U.S. Cl.
CPC ............ *A61F 9/00823* (2013.01); *A61B 2018/00916* (2013.01); *A61B 2018/2025* (2013.01); *A61B 2018/2205* (2013.01); *A61B 2090/502* (2016.02); *A61F 2009/00863* (2013.01); *A61F 2009/00897* (2013.01); *A61N 2005/0643* (2013.01)

(58) Field of Classification Search
USPC .......................................................... 606/4–5
See application file for complete search history.

(56) References Cited

U.S. PATENT DOCUMENTS

| | | | |
|---|---|---|---|
| 5,425,729 A | | 6/1995 | Ishida et al. |
| 5,480,396 A | | 1/1996 | Simon et al. |
| 5,488,443 A | | 1/1996 | Ota et al. |
| 5,514,127 A | | 5/1996 | Shanks |
| 5,543,866 A | | 8/1996 | Van de Velde |
| 5,568,208 A | | 10/1996 | Van de Velde |
| 5,599,340 A | * | 2/1997 | Simon ..................... A61F 9/008 606/4 |
| 5,743,902 A | | 4/1998 | Trost |
| 5,892,569 A | | 4/1999 | Van de Velde |
| 5,921,981 A | | 7/1999 | Bahmanyar et al. |
| 5,943,117 A | | 8/1999 | Van de Velde |
| 5,957,915 A | | 9/1999 | Trost |
| 5,971,978 A | | 10/1999 | Mukai |
| 5,980,513 A | | 11/1999 | Frey et al. |
| 6,066,128 A | | 5/2000 | Bahmanyar et al. |
| 6,096,028 A | * | 8/2000 | Bahmanyar ............ A61B 3/135 606/16 |
| 6,099,522 A | | 8/2000 | Knopp et al. |
| 6,149,644 A | | 11/2000 | Xie |
| 6,186,628 B1 | * | 2/2001 | Van de Velde ......... A61F 9/008 351/205 |
| 6,238,385 B1 | | 5/2001 | Harino et al. |
| 6,267,756 B1 | | 7/2001 | Feuerstein et al. |
| 6,328,733 B1 | | 12/2001 | Trost |
| 6,331,177 B1 | | 12/2001 | Munnerlyn et al. |
| 6,347,244 B1 | | 2/2002 | Dubnack |
| 6,489,589 B1 | * | 12/2002 | Alexander ............ A61C 1/0046 219/121.69 |
| 6,494,878 B1 | | 12/2002 | Pawlowski et al. |
| 6,789,900 B2 | | 9/2004 | Van de Velde |
| 7,146,983 B1 | | 12/2006 | Hohla et al. |
| 2001/0037105 A1 | | 11/2001 | Lin |
| 2004/0017545 A1 | | 1/2004 | Gutridge et al. |
| 2004/0039378 A1 | | 2/2004 | Lin |
| 2005/0080467 A1 | | 4/2005 | Abe |
| 2006/0004347 A1 | | 1/2006 | Altshuler et al. |
| 2006/0100677 A1 | * | 5/2006 | Blumenkranz ......... A61F 9/008 607/89 |
| 2006/0161145 A1 | | 7/2006 | Lin et al. |
| 2007/0129775 A1 | | 6/2007 | Mordaunt et al. |
| 2008/0015553 A1 | | 1/2008 | Zacharias |
| 2010/0249760 A1 | | 9/2010 | Blumenkranz et al. |
| 2012/0296320 A1 | | 11/2012 | Lin et al. |

FOREIGN PATENT DOCUMENTS

| | | |
|---|---|---|
| JP | 2005-118166 A | 5/2005 |
| JP | 2011-149403 A | 8/2011 |
| WO | 1999/53992 A2 | 10/1999 |
| WO | 2001/37769 A1 | 5/2001 |
| WO | 2005/065116 A2 | 7/2005 |

OTHER PUBLICATIONS

Office Action received for Japanese Patent Application No. 2008541299, dated Nov. 15, 2010, 3 Pages.

Office Action received for Japanese Patent Application No. 2008-541299, dated Jul. 12, 2012, 7 pages (3 pages of English Translation and 4 pages of Office Action).

Extended European Search Report received for European Patent Application No. 06827820.9, dated Nov. 2, 2009, 7 pages.

Office Action received for Japanese Patent Application No. 2008-541299, dated Oct. 17, 2011, 5 pages (2 pages of English Translation and 3 pages of Office Action).

International Preliminary Report on Patentability received for PCT Patent Application No. PCT/US2006/044296, dated May 20, 2008, 6 pages.

International Search Report received for PCT Patent Application No. PCT/US2006/044296, dated Aug. 3, 2007, 1 page.

\* cited by examiner

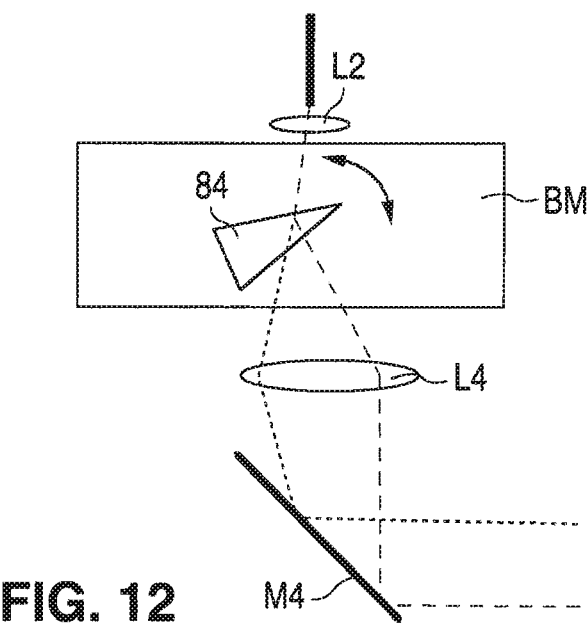
FIG. 12
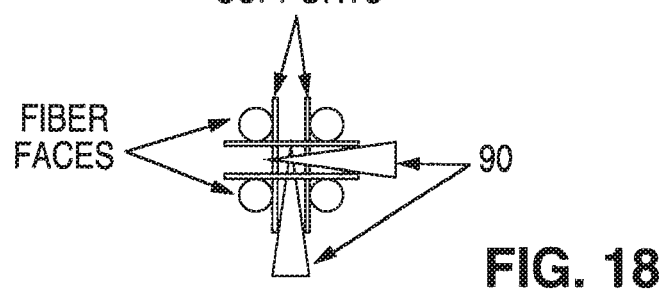
FIG. 18
 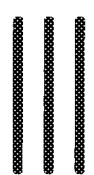 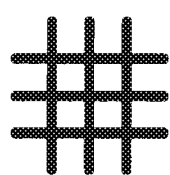 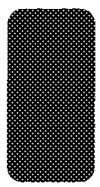
FIG. 19A  FIG. 19B  FIG. 19C  FIG. 19D
  
FIG. 19E  FIG. 19F  FIG. 19G

MULTIPLE SPOT PHOTOMEDICAL TREATMENT USING A LASER INDIRECT OPHTHALMOSCOPE

CROSS REFERENCE TO RELATED APPLICATION(S)

This application is a divisional of U.S. Ser. No. 11/595,423, filed on Nov. 8, 2006, which claims the benefit of priority under 35 U.S.C. § 119(e) of U.S. Ser. No. 60/737,548, filed on Nov. 16, 2005, which are each incorporated herein by reference in their entirety.

FIELD OF THE INVENTION

The present invention relates generally to patterned photothermal treatment of retinal tissue and particularly to such treatment using a laser indirect ophthalmoscope.

BACKGROUND INFORMATION

Conditions such as diabetic retinopathy and age-related macular degeneration are subject to photocoagulative treatment with laser light. While this type of laser light treatment slows the damage rate of the underlying disease, it has its set of problems. For example, because the treatment entails exposing the eye to a large number of laser light pulses for a long period of time (typically each pulse is on the order of 100 ms), damage can be caused to the patient's sensory retina from the heat that is generated. During the treatment, heat is generated predominantly in the retinal pigmented epithelium (RPE), which is the melanin-containing layer of the retina directly beneath the photoreceptors of the sensory retina. Although visible light is predominantly absorbed in the RPE, this type of treatment irreversibly damages the overlying sensory retina and negatively affects the patient's vision.

A slit-lamp-mounted laser delivery device is commonly used for this type of laser light treatment. In this device, the slit lamp is arranged to allow easy illumination and microscopic viewing of the eye of a seated patient. Slit lamps used in laser treatment/surgery include a high-brightness illuminator and microscope assemblies mounted on a shared pivot point. This arrangement allows the viewing angle of the microscope and illuminator to be changed as often as desired without moving the field of illumination or visualization transversely.

Slit-lamp-mounted laser delivery devices have their shortcomings. Specifically, certain parts of the eye are difficult to treat with this type of device. For example, the anterior aspect of a retinal break is by far the most important part to seal, as this is the area most subjected to vitreous traction. However, this area is not completely accessible with a slit-lamp-delivered laser system. Also, the slit-lamp-mounted laser delivery device is not well suited for treating small infants or bed-ridden patients. Furthermore, it is difficult to orient the patient's head position with slit-lamp-mounted systems. Thus, these devices have limited ability to treat patients with detached retinas and other conditions where gas or dense fluids have been introduced into the eye to secure detached tissues prior to laser exposure. To treat these conditions, the patient's head is oriented to reposition the tissue or tamponade material.

FIG. 1 shows a Laser Indirect Ophthalmoscope (LIO), which may be used in conjunction with the slit-lamp-mounted laser delivery device to overcome these shortcomings. As illustrated, the LIO 1 is worn on the physician's head using a headset 2 and is used to treat peripheral retinal disorders, particularly in infants or adults requiring treatment in the supine position. It is typically used in an operating room or clinical environment. Traditionally, an LIO 1 is used with a fiber optic coupled light source 3 attached to a beam delivery and visualization system 4 via an optical fiber 5, which is worn by a physician, to deliver treatment spots one at a time, with the physician moving his or her head and/or the ophthalmic lens to reposition the aiming beam prior to delivering another spot of treatment light. This is difficult and tiresome for both patient and physician.

Accordingly, there is a need for a flexible and time-efficient approach to retinal photocoagulation with an LIO that is not provided by known methods or apparatus.

SUMMARY OF THE INVENTION

The present invention is an improved device and method for patterned photothermal treatment of retinal tissue utilizing a laser indirect ophthalmoscope.

An apparatus for photomedical treatment or diagnosis of a target tissue includes a light source for generating light, a headset designed to be worn by a user wherein the headset includes an input for receiving the light and an output for projecting the light on a target tissue, and a beam multiplier positioned for receiving the light and for generating one or more optical beams by spatial and/or temporal separation of the light for projection thereof via the output on the target tissue in the form of a pattern.

A method of treating target tissue includes generating light, conveying the light to a head mountable LIO apparatus having an input for receiving the light and an output, converting the light to one or more optical beams in the form of a pattern using a beam multiplier that spatially and/or temporally separates the light, and projecting the pattern of the one or more optical beams to target tissue.

Other objects and features of the present invention will become apparent by a review of the specification, claims and appended figures.

BRIEF DESCRIPTION OF THE DRAWINGS

FIGS. 5, 6, 7, 8, 9, 10, 11, 12, 13, and 14 area schematic diagrams of a first, second, third, fourth, fifth, sixth, seventh, eighth, ninth, and tenth embodiments of the beam multiplier BM.

FIG. 18 shows a 2×2 fiber arrangement be adjusted to change the spot pattern size and spacing.

FIGS. 19A through 19G show exemplary shapes of the spots that may be formed with the photomedical system.

DETAILED DESCRIPTION OF THE INVENTION

Figure 1:
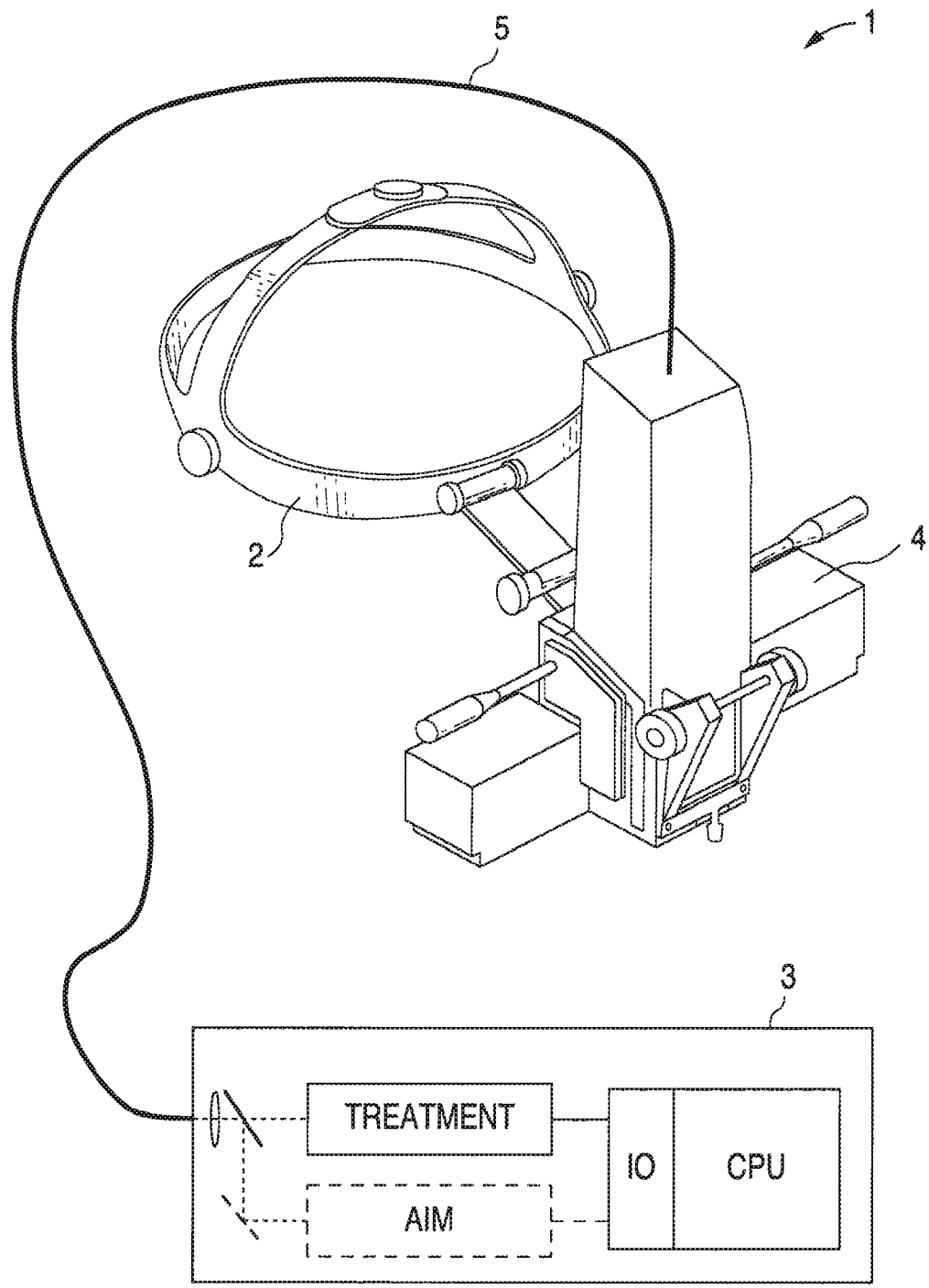
FIG. 1 shows a conventional Laser Indirect Ophthalmoscope (LIO).
Figure 2:
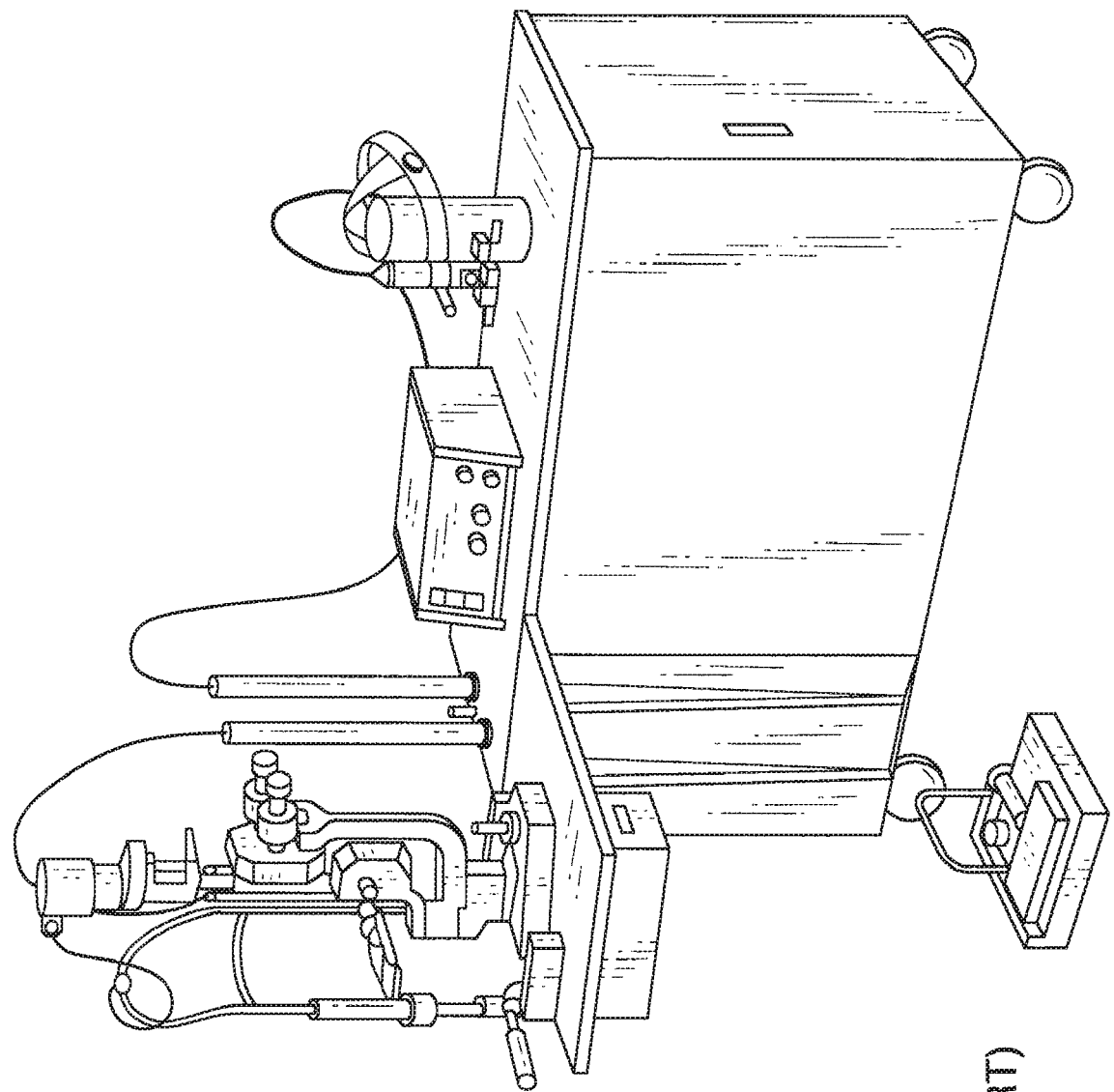
FIG. 2 shows a conventional slit-lamp delivery device.

Multiple spot laser therapy is known. For example, U.S. Pat. No. 4,884,884 by Reis discloses "beam multiplication" by various means. U.S. Pat. No. 5,921,981 by Bahmanyar and Jones discloses a slit-lamp based delivery device and intraocular probes only for multiple spot treatments. U.S. Pat. Nos. 6,066,128; and 6,096,028 by the same inventors cover only intraocular probes. However, multiple spot laser therapy is limited in application because it is performed utilizing slit-lamp delivery device (shown in FIG. 2), which has the disadvantages described above. An alternative way of performing multiple spot laser therapy is to utilize probes that are inserted into the eye. However, the use of probes is undesirable because of their intrusiveness.

This invention is based on multiple spot laser therapy using a Laser Indirect Ophthalmoscope (LIO). Using the LIO allows multiple spot laser therapy to be performed without intrusive probe insertions. Moreover, because the LIO allows the physician to treat patients in the supine position, the invention adds flexibility to multiple spot laser therapy.

Figure 3:
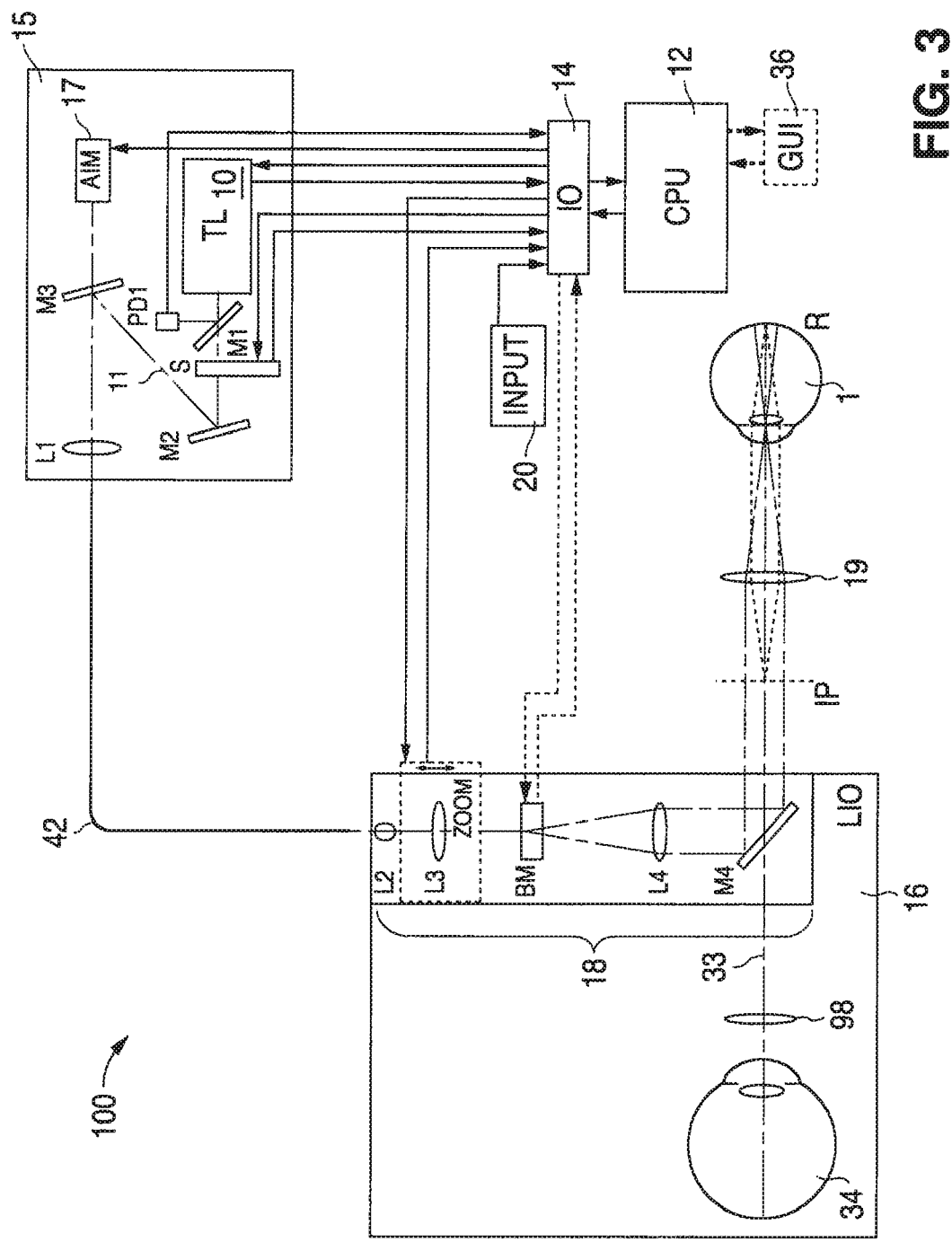
FIG. 3 is a schematic diagram of a photomedical system using a beam multiplier in accordance with a first embodiment of the invention.

FIG. 3 is a schematic diagram of a photomedical system 100 in accordance with a first embodiment of the invention. The photomedical system 100, which may be used for photomedical treatment or diagnosis, includes a CPU 12, an electronic input/output device 14, a light generation unit 15, and an LIO apparatus 16. The light generation unit 15 is optically coupled to the LIO apparatus 16 by a fiber unit 42. A user, such as a physician, wears the LIO apparatus 16 to view a target with his/her eye 34 through an ophthalmic lens 19. In this case, the target is the retina of an eye 1 (i.e., the patient's eye). The user 34 may see the eye 1 directly or through a screen, such as graphical user interface 36. The CPU 12 is coupled to the light generation unit 15 to control light generation. Optionally, the CPU 12 also controls the LIO apparatus 16. The CPU 12 may be a microprocessor, microcontroller, or any other type of suitable control electronics.

The light generation unit 15 includes a light source 10. The light source 10 may be a diode-pumped solid state laser, gaseous laser, semiconductor laser, light emitting diode, flash lamp, etc. The light source 10 is controlled by the CPU 12 via the input and output (I/O) device 14 to create an optical beam 11, whose centerline is shown by dashed lines. The optical beam 11, upon being generated by the light source 10, encounters mirror M1 which directs a first portion of the optical beam 11 to a photodiode PD1. The photodiode PD1 may be replaced with other types of sensors, as appropriate. The photodiode PD1 serves to sample and measure the power of the light for safety purposes. A second portion of the light from the mirror M1 that is not directed to the photodiode PD1 goes to a shutter S, which acts as a gate to the optical beam 11. The shutter S controls the optical beam 11 to produce discrete spots or a continuous supply of the optical beam to create continuous scans as a means to produce the desired pattern. If the shutter S blocks the light, the optical beam 11 does not travel further. On the other hand, if the shutter S lets the light pass, the optical beam 11 goes on to mirror M2 and mirror M3. Mirror M2 is a turning mirror that may be used in conjunction with mirror M3 to align the optical beam 11 into the fiber unit 42.

Multiple spot laser therapy may be performed using an optional aiming beam in addition to a treatment beam. The aiming beam is used to indicate the location of the beam on the target tissue 1. It may be coincident upon the treatment beam, or provide an outline (or other indication) of the area to be treated. Where an aiming beam is used in addition to the treatment beam, the optical beam 11 generated by the light source 10 is the treatment beam, and a separate aiming beam is produced by an aiming light source 17. The aiming light source 17 preferably produces light of a different wavelength than the light source 10. Once the treatment beam is aligned with the aiming beam, the treatment beam is delivered for treatment of the eye. Each of the aiming beam and the treatment beam may include a single spot of light, multiple discrete spots, or continuous pattern(s) of light.

The aiming beam and the optical beam may be interleaved by gating the light beams on and off. Each spot of light may be round or have some other shape. The aiming beam and the treatment beam do not need to be produced simultaneously. Mirror M3 combines the aiming beam with the optical beam 11 and directs the combined light into the fiber unit 42 via the lens L1. The lens L1 is used to inject the optical beam 11 into the optical fiber unit 42.

Although use of an aiming beam is contemplated as an option, the description herein will focus on the optical beam 11 for simplicity of illustration. Where an aiming beam is used, the optical beam 11 that is received by optical fiber unit 42 is a combination of the aiming beam and the treatment beam.

If the light source 10 produces visible (or otherwise aim quality) light, it may also be used for producing the alignment pattern, making a separate aiming light source 17 unnecessary. The alignment pattern coincides with portions of the eye 1 that will later be illuminated with the optical beam 11 and ensures that the system is properly aligned to the target portion(s) of the eye 1.

The optical beam 11 is transmitted to the LIO assembly 16 via an optical fiber unit 42. A pattern generator assembly 18, where lens L2 acts as the optical input for receiving the optical beam, and mirror M4 acts as the optical output for projecting the beam onto the target tissue, in the LIO apparatus 16 receives the optical beam 11 and directs the optical beam 11 toward the target—i.e., the retina R of the patient's eye 1. The optical beam 11 is focused on the eye 1 and perceived by the patient. A pattern (which may be predetermined) is disposed at the patient's retina R. The position and character of the pattern may be controlled by use of an input device 20 (e.g., a remote control panel) or other user interface, such as graphical user interface (GUI) 36. A person of ordinary skill in the art would understand that the disposition of the optical beam 11 is a function of the optics of the photomedical system 100 and any particular conditions of the patient. Particular conditions that may affect the ultimate disposition of the optical beam 11 include cataracts, retinal inhomogeneities, and intraocular debris, among others.

Lenses L2, L3, and L4 of the pattern generator assembly 18 function to condition and direct the optical beam 11 to the patient's eye 1. Light exiting the optical fiber unit 42 first encounters lens L2 and becomes, for example, collimated before entering the lens L3. Lens L3 may be a single lens or a compound lens, and can be configured as a zoom lens for adjusting the intrinsic size of the beam that comprises the pattern. The light coming out of the lens L3 passes through the beam multiplier BM and enters the lens L4. The beam multiplier BM produces a pattern of multiple spots or a scanned pattern.

When the mirror M4 is small, it may be placed directly in the visualization path 33 without much disturbance. Mirror M4 may also be placed in the center of a binocular imaging apparatus without substantially disturbing the visualization. Lens L4 could also be placed one focal length away from the optical midpoint of the scanning optics to produce a telecentric scan, such as is required for optimal performance by certain choices of ophthalmic lens 19. In this case, the mirror M4 would need to be large enough to contain the entire scan, and could be made as a high reflector spectrally matched to the output of light sources 10 and 17, if used. Visualization 34 of the target zone of the eye is accomplished by viewing through the mirror M4. A further refinement would be to white balance the transmission of mirror M4, making it photopically neutral, by using a more complicated optical coating that makes the transmitted image appear more natural rather than, for example, pinkish when using a green notch filter coating on mirror M4 as would be required when light source 10 produces green light. Visualization system 98 is contained in the LIO assembly 16, and allows the user to visualize the retina R of patient eye 1, preferably with both eyes of the user.

In some embodiments, the CPU 12 also controls the movement of mirror M4 thus controlling the location of the beam/pattern on the target tissue 1. The optical scan to form the pattern can be created in a number of different ways, such as by moving the light source 10, moving the mirror M4, using one or more rotating wedges, using acousto-optic deflector(s), or galvanometric scanner(s), etc. Preferably, mirror M4 may be rotated as already described, or in the case of a mirror with Surface curvature (optical power), it may also be translated to produce optical deviation. In the case where mirror M4 has optical power, compensating optical elements (not shown) may be required to produce an image, as opposed to simple illumination as shown. The perception of both discrete spots and spot blinking may be accomplished by scanning quickly between elements of the pattern so as to limit the amount of light registered by the patient and observed in those intermediate spaces.

The pattern may also be used to fixate the patient so that the patient looks at a fixed position away from the optical axis of the physician's visualization and light delivery system, thereby keeping the patient's eye still, and also providing the physician direct optical access to the retinal periphery. Small motions of the pattern may be used to minimize actual eye movement while still capturing the patient's attention. This technique may be especially useful in situations such as pan retinal laser photocoagulation treatment where slight eye movement can be tolerated. Slightly moving the pattern about a center position to attract the patient's attention makes it easy for the patient to fixate on the pattern. Ensuring fixation is especially important during procedures such as macular grid laser photocoagulation treatment, where unintended laser exposure to the central vision is to be avoided.

The ophthalmic lens 19 aids in the user 34 visualization of the retina and creates a magnified intermediate image of retina R at location IP. The ophthalmic lens 19 may then serve to help relay the beam/pattern to retina R. The beam thus relayed to the target tissue 1 will be magnified by the inverse of the image magnification of ophthalmic lens 19. The ophthalmic lens 19 may be a contact or non-contact lens, and may also be used in conjunction with the lens L4 to provide for conjugate pupil planes such that the scanning pivots about the patient's iris, thus maximizing the system's retinal scan field.

Figures 4A, 4B, 4C:
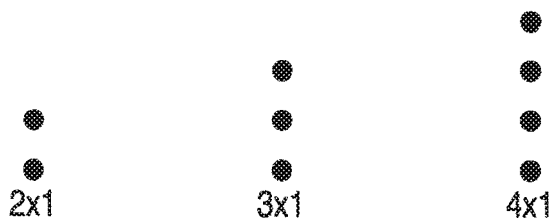
FIGS. 4A through 4I illustrate examples of laser spot patterns that can be generated by the photomedical system of the invention.
Figures 4D, 4E, 4F:
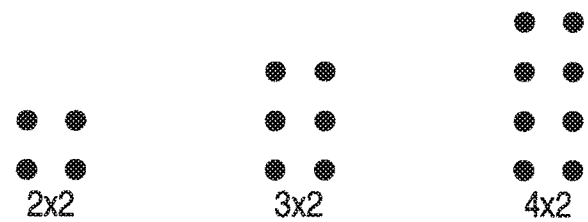
Figures 4G, 4H, 4I:
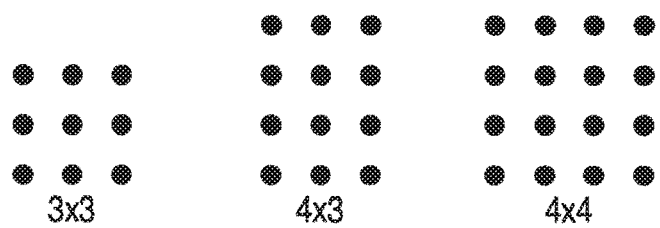

FIGS. 4A through 4I illustrate examples of laser spot patterns that can be generated by the photomedical system of the invention. The spots in a pattern are of equal irradiance, size, and separation. FIGS. 4A, 4B, and 4C show linear arrays (e.g., 2×1, 3×1, 4×1) and FIGS. 4D through 4I show two-dimensional arrays (e.g., 2×2, 3×2, 4×2, 3×3, 4×3 and 4×4). Other patterns may also be generated, such as a circular pattern that may be used to encircle retinal tears. The edge-to-edge separation distance between spots typically varies from 0.5-3 times the spot diameter. For example, a separation distance of 0.5 times the spot diameter may be used for encircling retinal tears, while a separation distance of 3 times the spot diameter may be used for treating lattice degeneration.

There are different ways the beam multiplier BM may produce multiple spots. One way of producing multiple spots is to employ the beam multiplier BM in the LIO assembly 16 as shown in FIG. 3. The LIO assembly 16 is worn by the user 34 (e.g., physician, surgeon) using conventional head mounting hardware. The beam multiplier BM may contain active and/or passive components. The beam multiplier BM may or may not be controlled by the CPU 12 (e.g., a passive element such as a diffractive optic could be used). Thus, in FIG. 3, the connection between the beam multiplier BM and the system is shown with dashed lines. The beam multiplier may be changed or adjusted to alter the spot pattern and/or the orientation of the pattern. The beam multiplier BM may be rotated to re-orient the pattern. This may be performed automatically via CPU 12. Additional optics may also be used to rotate the pattern orientation, such as a Dove prism, not shown. Alternately, beam multiplier BM may be incorporated into the light generation unit 15, and delivered to the pattern generator assembly 18.

Figure 15:
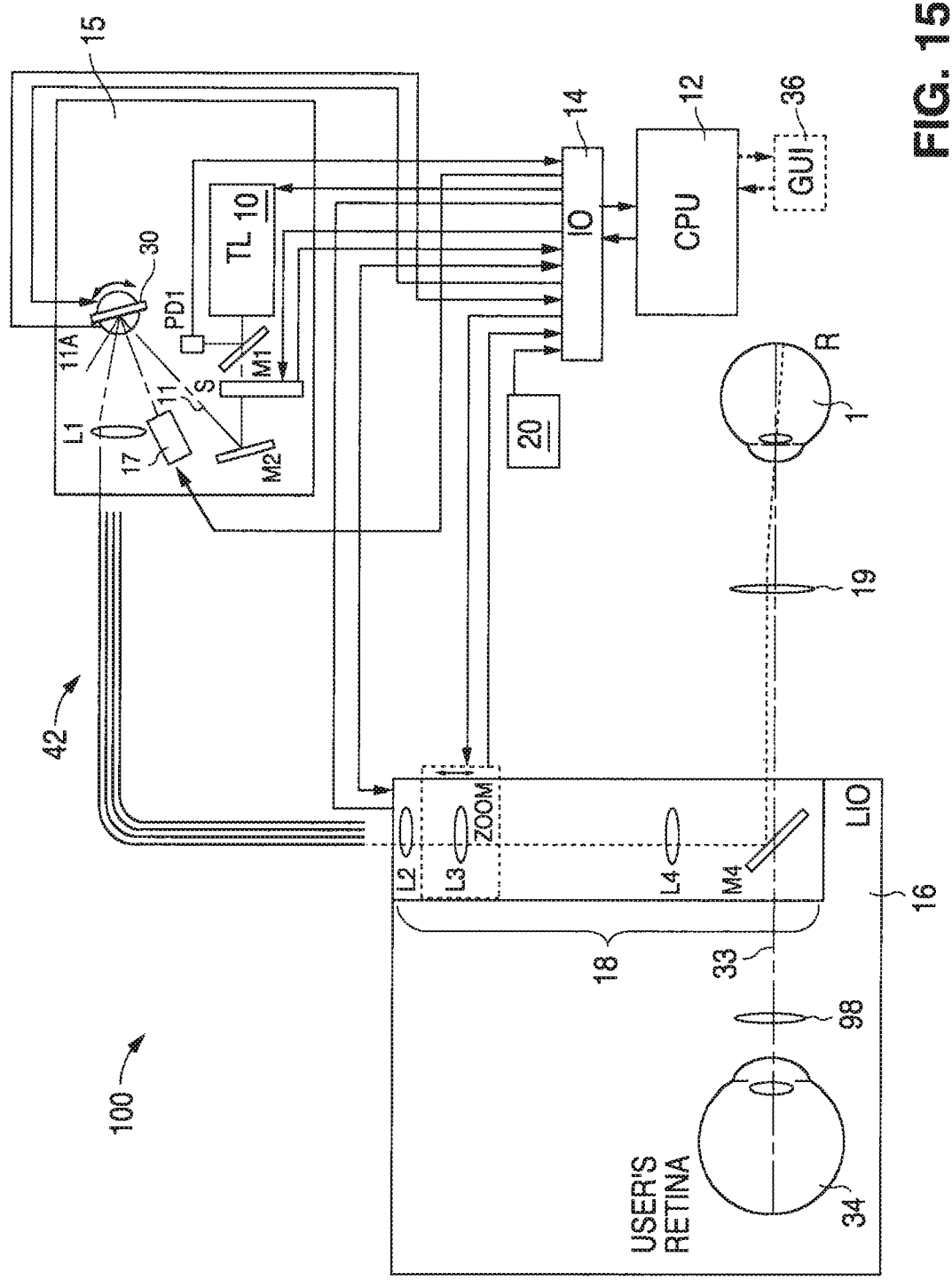
FIG. 15 is a second embodiment of the photomedical system using a fiber bundle to deliver multiple spots.
Figure 16:
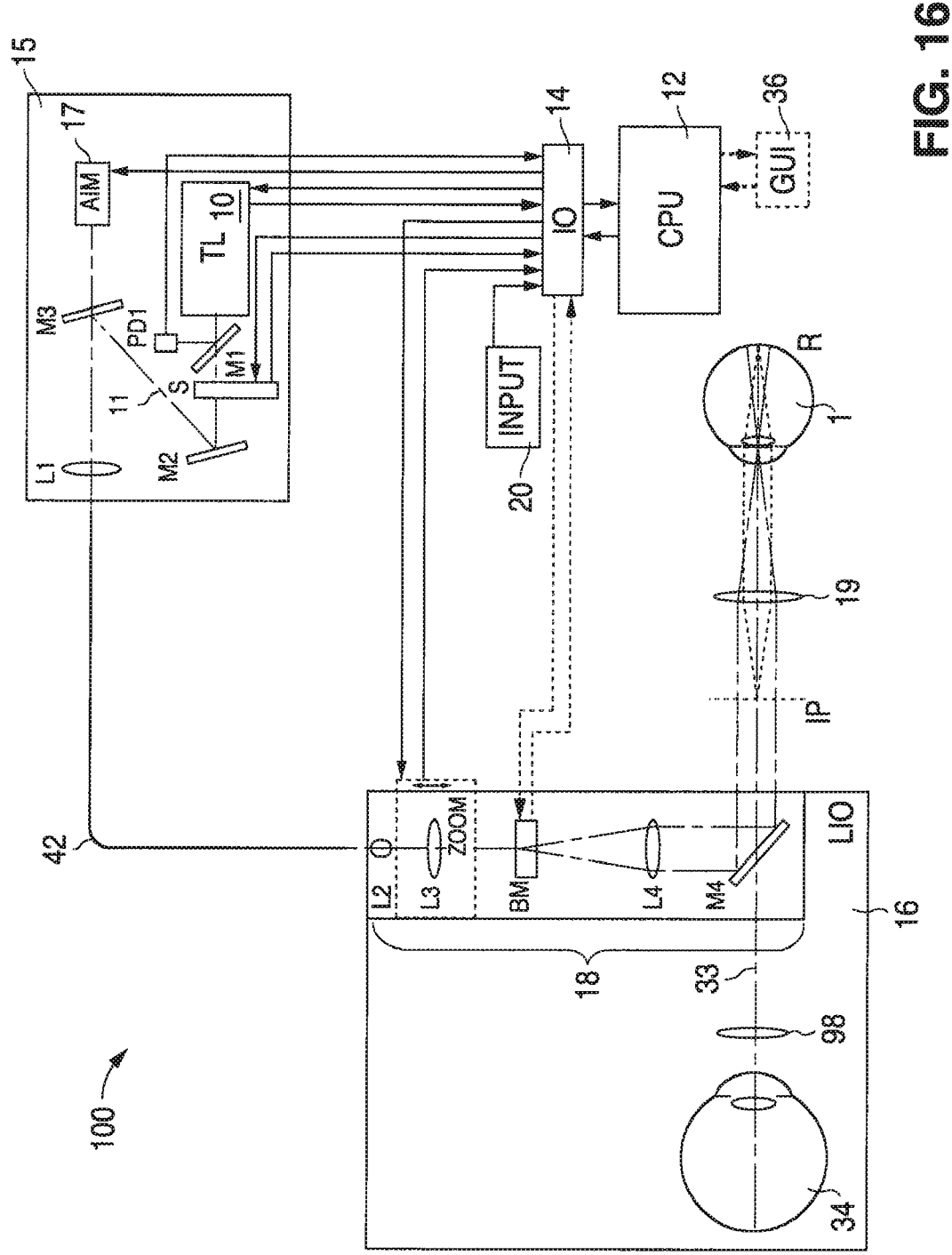
FIG. 16 is a third embodiment of the photomedical system whereby the fiber unit is a fiber bundle.
Figure 17:
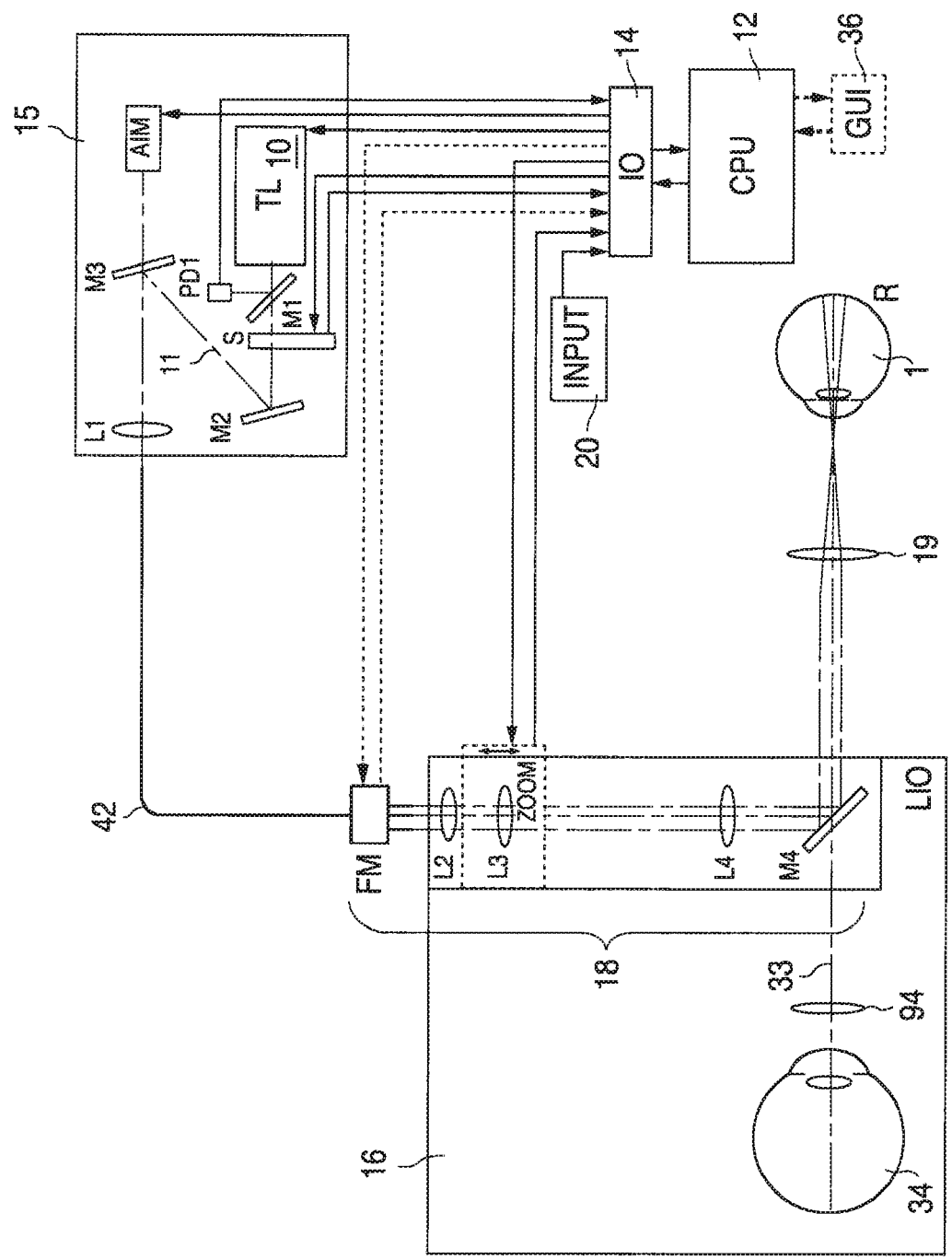
FIG. 17 is a fourth embodiment of the photomedical system whereby the fiber unit contains a fiber multiplier.
Figure 20:
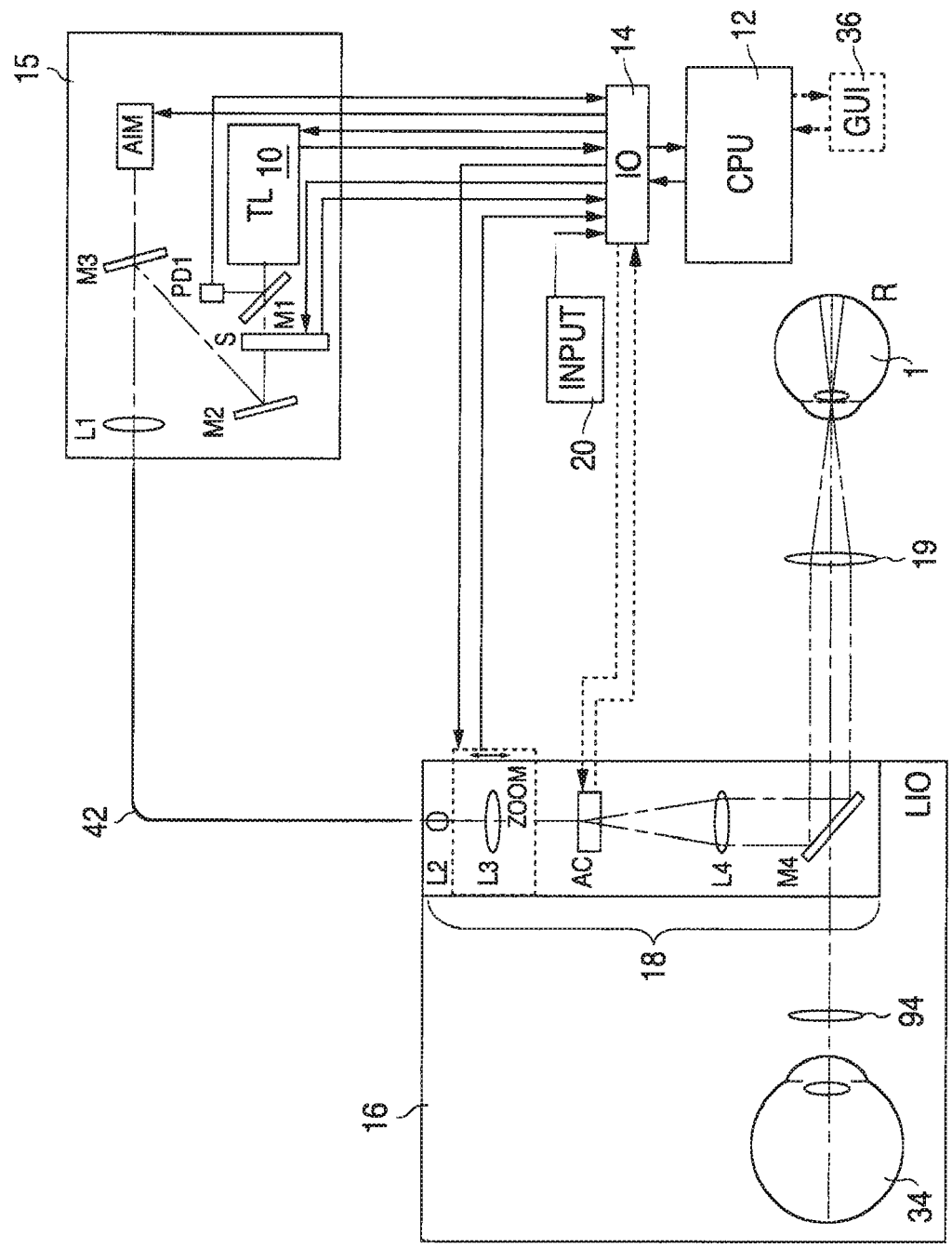
FIG. 20 is a fifth embodiment of the photomedical system using an anamorphic element AC.

The beam may be multiplied simultaneously, scanned to ultimately produce a pattern of delivered spots, or both. Thus, as used herein, "beam multiplication" by beam multiplier BM applies to simultaneous beam multiplication (e.g., by dividing a beam into multiple sub-beams—spatial separation), beam scanning (e.g., beam spots or pattern are projected or formed sequentially—temporal separation), or any combination of the two. FIGS. 5, 6, 7, and 12 show embodiments of the beam multiplier BM that generates the pattern primarily by scanning. FIGS. 8, 9, 10, 11, 13, and 14 show embodiments of the beam multiplier BM that generates a pattern primarily by dividing a beam into multiple sub-beams. FIGS. 15, 16, and 17 show embodiments of the photomedical system 100 that generate the pattern using multiple fibers connected to the light generation unit 15. FIG. 20 shows an embodiment of the photomedical system 100 that anamorphically generates the pattern. In FIGS. 5-14, the lens L3 is not always explicitly shown; however, a person of ordinary skill in the art will understand that the lens L3 may sometimes be needed for adjusting the ultimate size of the optical beam on the target tissue.

Figure 5:
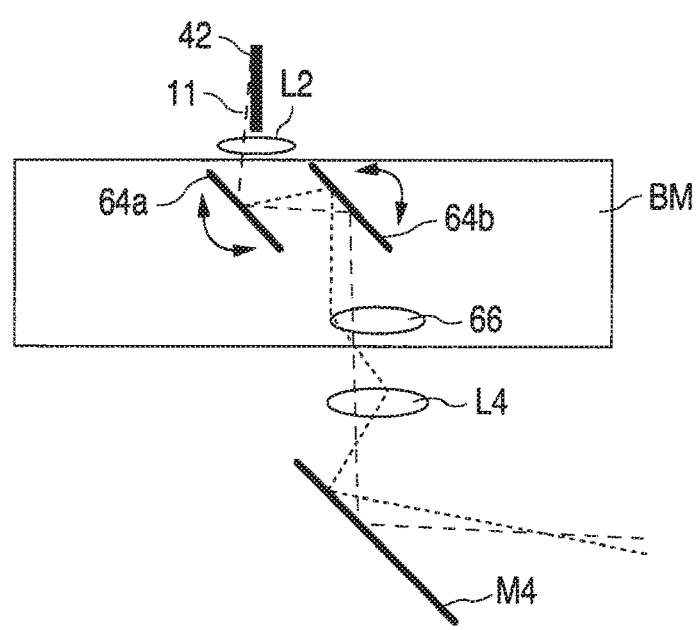

FIG. 5 is a schematic diagram of a first embodiment of the beam multiplier BM. In this embodiment, the beam multiplier BM is made with active components such as one or more mirror-based galvanometric scanners. This first embodiment includes a pair of orthogonal axis galvanometric scanners 64a, 64b. The lens L2 conditions optical beam 11 prior to its incidence upon the first scanner 64a, which directs the optical beam 11 toward the second scanner 64b. As the scanner 64a moves, it reflects the optical beam 11 in different directions. Beams that are reflected in different directions strike the second scanner 64*b* at different locations, and are reflected by the second orthogonal axis scanner 64*b* onto different locations on the lens IA. Lens 66 may serve to further condition the beam exiting the scanners, for example, for the purpose of aberration control, but is not necessarily required. The beams reach the lens L4 at different locations and angles. In the case of a telecentric scan, where the midpoint between the scanners 64*a* and 64*b* is located nominally one focal length away from lens L4, the beams reach the mirror M4 at different points and are reflected toward the image of the target tissue provided by ophthalmic lens 19 as shown in FIG. 3. When the timing of the laser pulses is coordinated with the angular position of the mirrors of the scanners 64*a* and 64*b*, separate beams (i.e., multiple spots) are created. However, if the light source 10 were left to run continuously, a likewise continuous pattern may be created.

Figure 6:
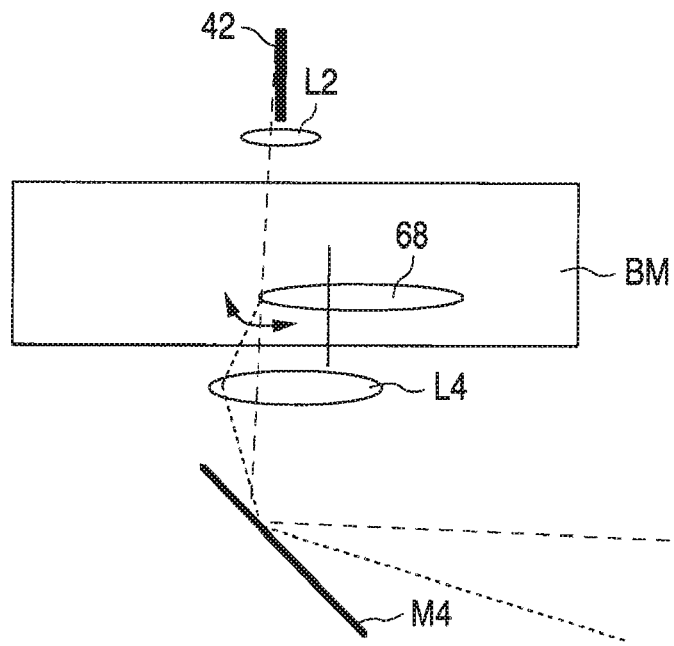

FIG. 6 is a schematic diagram of a second embodiment of the beam multiplier BM. In this embodiment, the beam multiplier BM includes an optical element with focusing power, specifically an off-axis moving lens 68 that is movable transversely to the optical axis and able to rotate eccentrically (i.e. not about its optical axis). As the lens 68 spins, the optical beam 11 coming from the lens L2 reaches different parts of the lens 68, thus getting refracted differently depending on what portion of the lens 68 is encountered. The lens L4 directs the optical beam 11 coming from different angles emanating from lens 68 to different spots on the mirror M4. The lens 68 may be replaced with a mirror in other embodiments, where different portions of the moving lens 68 would reflect the beam at different angles.

Figure 7:
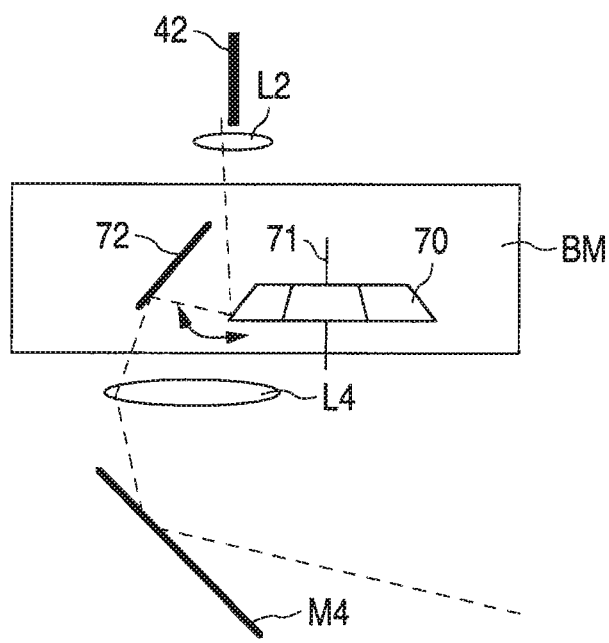

FIG. 7 is a schematic diagram of a third embodiment of the beam multiplier BM. In this embodiment, the beam multiplier BM includes a rotating reflective polygon scanner 70 and a reflective element 72. The rotating polygon 70 may be configured to provide different deviation angles on different facets. As the polygon rotates about an axis 71, the optical beam 11 coming from the lens L2 hits different points on the polygon 70 and leaves the polygon 70 at different angles. The reflective element 72 receives the optical beam 11 from the polygon 70 and directs it to the lens L4. The lens L4 forwards the optical beam 11 to the mirror M4. The position on the mirror M4 that the optical beam 11 strikes differs depending on which part of the polygon 70 reflects the optical beam 11.

Figure 8:
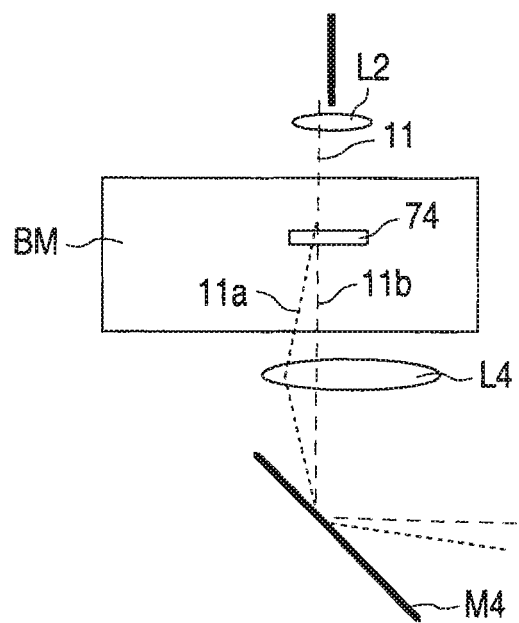
Figure 9:
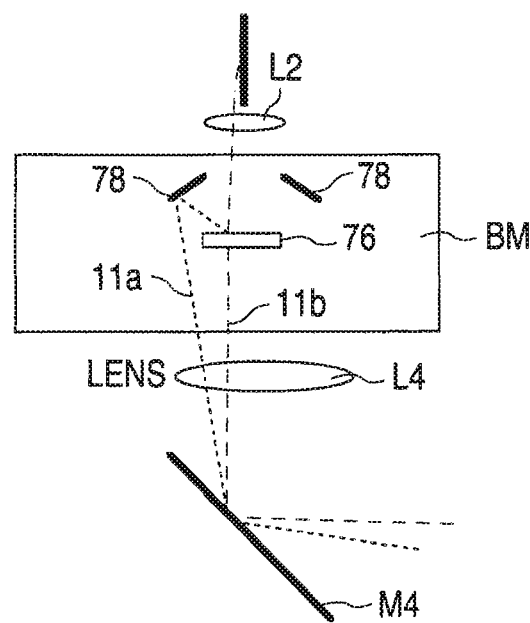

FIGS. 8 and 9 are schematic diagrams of fourth and fifth embodiments of the beam multiplier BM, respectively. The fourth and fifth embodiments utilize diffraction elements. In FIG. 8, the beam multiplier BM includes a transmissive diffraction element 74, which could be an acousto-optic deflector, hologram, a grating, a phase array, or an adaptive optic, for example. The optical beam 11 coming from the lens L2 reaches the transmissive diffraction element 74 and gets divided into sub-beams 11*a*, 11*b* which strike the mirror M4 in different places, and/or at different incident angles.

In FIG. 9, the beam multiplier BM includes a reflective diffraction element 76 along with reflective elements 78. The optical beam 11 coming from the lens L2 reaches the reflective diffraction element 76 to get divided into sub-beams 11*a*, 11*b*. The reflected sub-beams 11*a*, 11*b* are redirected toward the lens IA by one of the reflective elements 78. Eventually, the sub-beams 11*a*, 11*b* strike the mirror M4 and propagate toward the eye 1 along separate paths.

Using diffractive or refractive elements to deviate the beam yields different results for different wavelengths. This sensitivity to wavelength complicates the use of a different-colored aiming beam and multi-spectral treatment sources. Thus, when more than one wavelength is used, such as in the case of FIG. 9, another dispersive element may be used to compensate for the difference in results. An adaptive optic may also be used to directly create matching patterns for treatment and aiming light by rewriting its configuration for each wavelength. Such a device would also allow for the straightforward adjustment of the pattern, provide simultaneous and/or sequential beam multiplication, and even be made to also focus the beam(s). A lens array or a diffractive optical element placed in the optical system provides a plurality of simultaneous spots.

Figure 10:
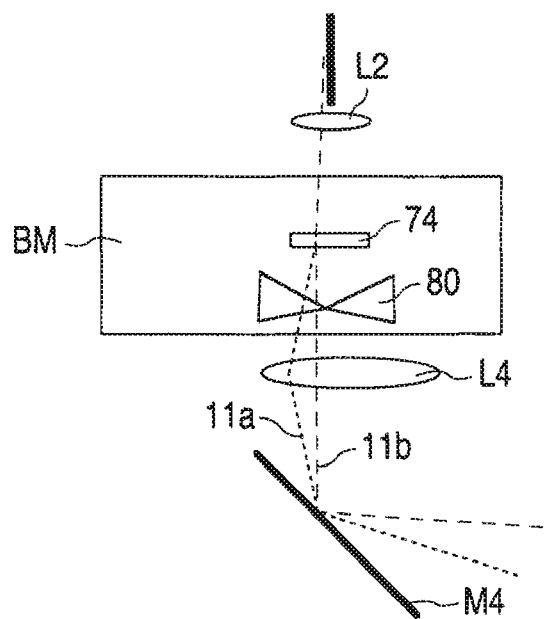
Figure 11:
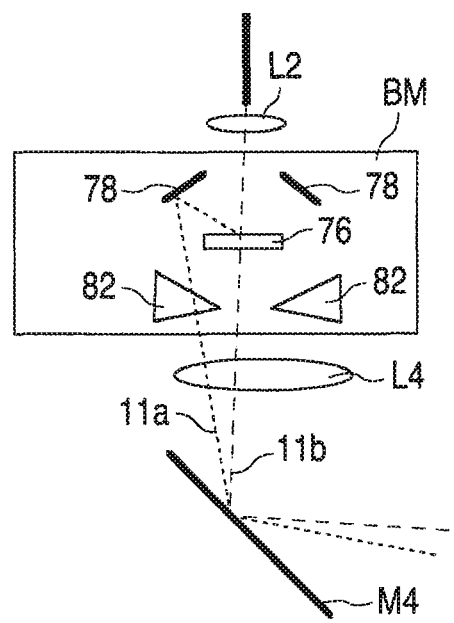

FIGS. 10 and 11 are schematic diagrams of a sixth and seventh embodiments of the beam multiplier BM, respectively. The sixth and seventh embodiments utilize transmissive and reflective diffractive elements with dispersion compensation. The embodiment of FIG. 10 is substantially similar to the embodiment of FIG. 8, with the addition of a dispersion compensation element(s) 80. The embodiment of FIG. 11 is substantially similar to the embodiment of FIG. 9, with the addition of dispersion compensating elements 82. The dispersion compensating elements 80, 82 may be high dispersion prisms or tilted plates, such as those made from flint glasses or plastics.

The components described in FIGS. 5 through 11 may be used in any combination not explicitly shown here.

FIG. 12 is a schematic diagram of an eighth embodiment of the beam multiplier BM, whereby the beam multiplier BM includes a prism 84. The prism 84 rotates (as shown by the arrow) so that the optical beam 11 coming from the lens L2 strikes at a different incident angle on the prism 84 and experiences a different degree of refraction depending on how it strikes the prism 84. The prism may also be made to rotate about the optical centerline of the system to create 2-dimensional patterns. The optical beam 11 that is refracted passes through the lens L4 to reach the mirror M4.

Figure 13:
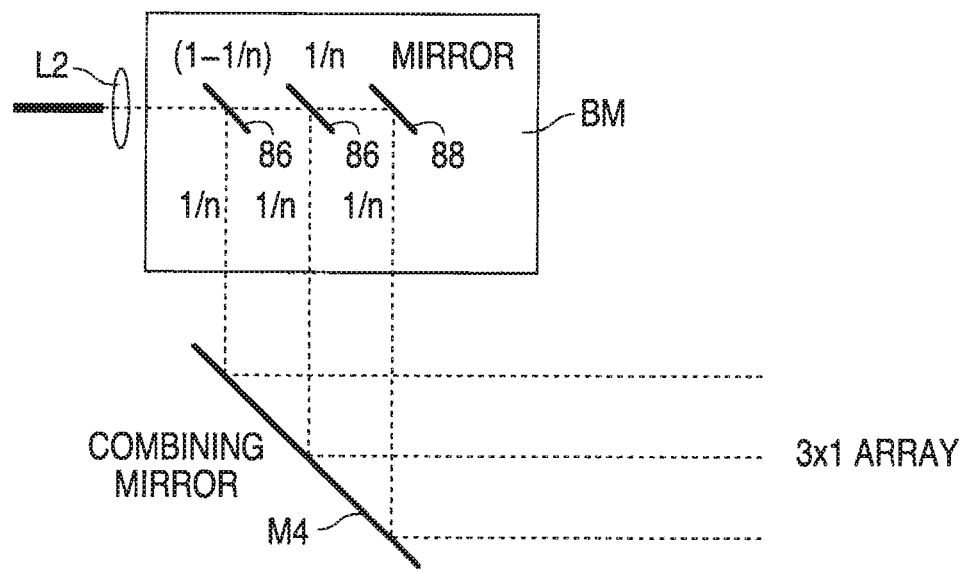
Figure 14:
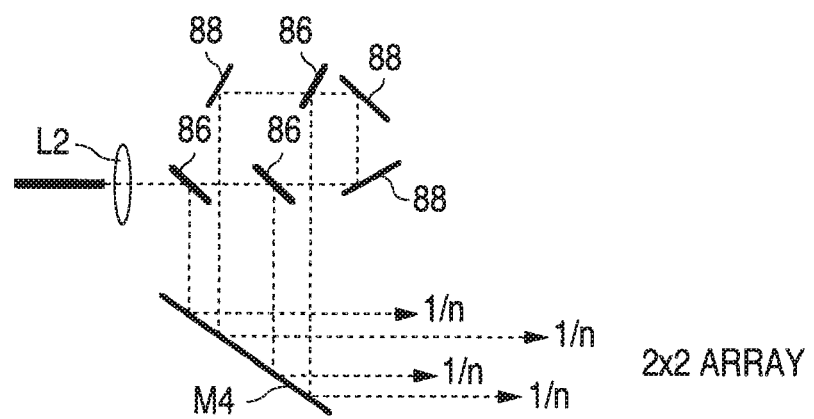

FIG. 13 and FIG. 14 show ninth and tenth embodiments of the beam multiplier BM utilizing reflective elements. In FIG. 13, the beam multiplier BM includes 2 beamsplitters 86 and a mirror 88. The optical beam 11 reaches the first beamsplitter 86, which directs a fraction ⅓ of the optical beam 11 to the mirror M4 and allows the remaining portion of the optical beam 11 to pass to the second beamsplitter 86. The second beamsplitter 86 then directs a fraction ½ of the beam it received toward the mirror M4. The remaining optical beam 11 is reflected toward the mirror M4 by the mirror 88. Although n=3 in the example of FIG. 13 that produces a 3×1 array pattern, this is not a limitation of the invention and n may be any integer that produces the pattern. To equally distribute the optical power amongst the spots of the pattern, the reflectivity of an individual beamsplitter 86, $R_i$, in an array of m=n−1 beamsplitters 86, is given by the relation, $R_i=(m-i+2)^{-1}$, where i is the number of the individual beamsplitter in the array, starting with i=1 for that nearest incoming light. Of course, in this configuration the reflectivity of the last beamsplitter will always be 50%. Lens L2 may serve to collimate the beam, thus allowing for the elements of the pattern to be focused onto a plane at the target by a subsequent lens, such as lens L4 shown in FIGS. 3, 5-12.

FIG. 14 shows an embodiment of the beam multiplier BM wherein the beamsplitters 86 and the mirrors 88 are arranged to produce a two-dimensional array pattern. In this embodiment, n=4 although this is not a limitation of the invention. The optical beam 11 reaches the first beamsplitter 86, which directs about ¼ of the optical beam 11 to the mirror M4 and passes the remaining portion of the optical beam 11 to the second beamsplitter 86. The second beamsplitter 86 directs another ¼ of the optical beam 11 to the mirror M4. The remaining ½ of the optical beam 11 gets reflected off two mirrors 88 to travel in a direction that is the opposite of the original direction in which the optical beam 11 entered the beam multiplier BM and is out of the plane of the illustration of FIG. 14. For simplicity, the illustration of FIG. 14 is depicted in one plane. Traveling in this reverse direction, the optical beam 11 encounters one more beamsplitter 86, which directs about ¼ of the original optical beam 11 to the mirror M4 and finally another mirror 88. The result is a 2×2 matrix pattern. Many such possibilities exist for creating other patterns. Again, here the same relation described above holds for $R_i$.

FIG. 15 is a second embodiment of the photomedical system 100 whereby a bundle of optical fibers 42 is used to deliver multiple spots sequentially. A fiber bundle that has its individual fibers separated at the input end can have a scanner positioned prior to fiber input such that it will direct the optical beam 11 to an individual fiber alone, ultimately providing a sequential pattern of spots by switching between the individual fibers. Alternately, the fiber bundle 42 may have more than a single fiber illuminated at a time to produce groupings of simultaneous spots. Sequential scanning of such simultaneous spots is also possible. The scanning element 30 (e.g., galvo mounted mirror(s)) is used to direct light to a single fiber of the bundle at any given time. The scanning element 30 may be spaced about one focal length away from lens L1 to provide for a telecentric scan condition, thus allowing for the injection of light into all the fibers to be on parallel paths and preserving the launch numerical aperture across the bundle. Such a bundle, or array, of fibers may be made to have its constituent fiber's input ends lie along a line for simplified single axis scanning (as shown), or be a 2-dimensional array accessed using a 2-dimensional scanner. The positions of the output ends of the fibers of the fiber bundle ultimately define the pattern.

FIG. 16 shows a third embodiment of the photomedical system 100 whereby a fiber bundle 42 is used to deliver multiple spots simultaneously. The optical beam 11 leaving the light generation unit 15 fills the individual fibers in the bundle simultaneously. Light output from this fiber bundle 42 will provide a pattern of simultaneous spots onto target tissue 1. The optical system of pattern generator assembly 18 may be made to image the face of the fiber bundle onto the target tissue (say via the intermediate image created by ophthalmic lens 19).

FIG. 17 is a fourth embodiment of the photomedical system 100 where a single fiber is used with a fiber multiplier as part of the fiber unit to provide delivery of multiple spots. A passive fiber splitter may be used to distribute light into multiple fibers simultaneously, or an active fiber switch may be used to sequentially vary which fiber conducts the light. This fiber multiplier is labeled "FM" and shown with dashed lines connecting it to the CPU 12. The output ends of the individual fibers are distributed prior to lens L2. This distribution may be maintained in the final disposition of the spots on the target tissue.

FIG. 18 shows an example of how a 2×2 fiber multiplier FM can be adjusted to change the spot pattern size and spacing. In FIG. 18, wedges 90 are driven in and out to achieve different fiber spacing. The delivered pattern is moved or altered as a result of the wedges 90 being driven in and out. Similarly, a single conical element may be driven into the center of the fiber output array, thus varying the spacing uniformly with only a single adjustment.

The device of the invention allows the treatment time to be reduced by a factor that is approximately equal to the number of pulses delivered, whether the pulses are delivered simultaneously or sequentially. Simultaneous delivery has the advantage of being faster than sequential delivery, but requires a light source capable of delivering n times the output power, wherein n is the number of elements in the pattern. Sequential delivery, while being slower than simultaneous delivery, places less demand on the power of the light source and provides flexible adjustment of the ultimate delivery pattern. Both simultaneous and sequential deliveries with the device of the invention significantly reduce the treatment time and the placement precision of the lesions when compared to the manual technique that is conventional today. The eye can be considered stationary for approximately one second, the "fixation time." The number of spots that can be delivered sequentially in this fixation time is inversely proportional to their pulse duration.

FIGS. 19A through 19G show exemplary shapes of the spots that may be formed with the photomedical system 100. As shown, the shapes include one or more lines, a rectangle, one or more arcs, or a large arc area. These patterns/shapes may be generated, for example, by scanning a continuous beam or providing a beam-shaping device such as an adjustable aperture, or adaptive optic such as a liquid crystal matrix, or using anamorphic optical elements, such as cylindrical lenses, to create the desired shape instantaneously.

FIG. 20 is a fifth embodiment of the photomedical system 100. In this embodiment, the beam multiplier BM includes an anamorphic element AC. The anamorphic element AC allows the optical beam 11 to be anamorphically adjusted to provide an immediate beam shape on the target tissue that is different from the beam shape of the original optical beam 11. For example, even if the original optical beam 11 would have produced a circular spot, the anamorphic element AC is capable of producing the shapes shown in FIGS. 19A-19G. Conversely, even if the original optical beam 11 would have produced a non-circular spot, the anamorphic element AC is capable of producing a circular spot. The anamorphic element AC may be an adaptive, torroidal, or cylindrical optic. The anamorphic element AC is shown as connected to the CPU 12 with a dashed line because it may be either an active or a passive device.

Figure 21:
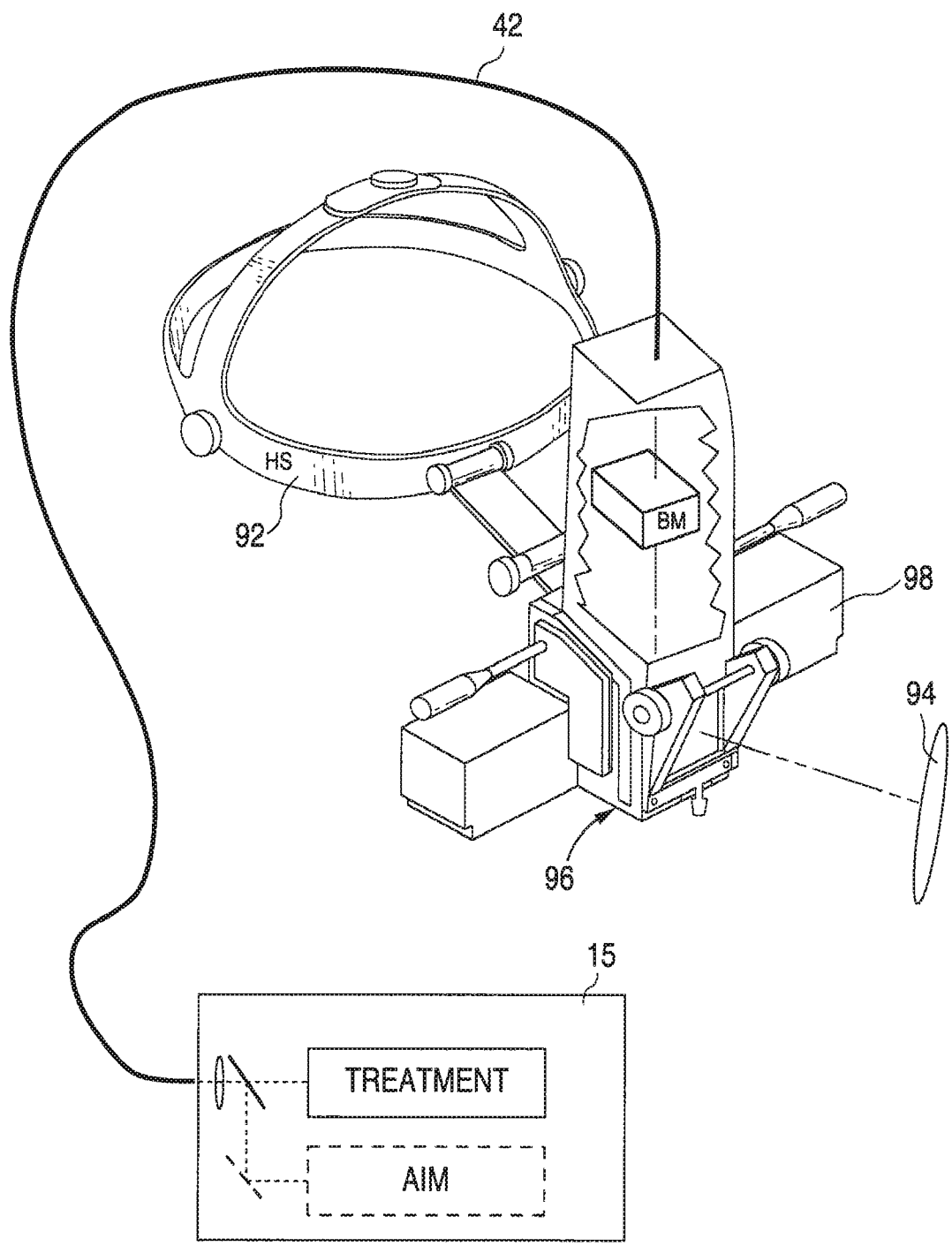
FIGS. 21 and 22 are a schematic representation of the photomedical system 100 illustrating the LIO apparatus.

FIG. 21 is a schematic representation of the photomedical system 100 illustrating the LIO apparatus 16. In the embodiment that is shown, the beam multiplier BM is contained in a housing that may or may not include the indirect ophthalmoscope illumination light (not shown). As described above, the beam multiplier BM may produce multiple spots either simultaneously or sequentially by a number of different means. The device is worn on the head using a headset 92, and the patient's fundus (not shown) is viewed through visualization system 98 (typically a binocular assembly) using the illumination (not shown) provided from the headset 92. An external light source may also be used for the visualization illumination. The treatment beam is also provided directly to the headset 92 via fiber optic connection 42 from the light generation unit 15. Optionally, the light generation unit 15 may also contain an aiming light 17 to display where a spot or a pattern of spots will be ultimately disposed on the target tissue. Alternatively, a pattern alignment target 96 (shown here with dotted lines to indicate it as an option) may be used in the optical path of the visualization system 98, and thus only visible to the physician. The pattern alignment target 96 may be made removable or interchangeable to allow for different patterns to be used. Each pattern alignment target 96 would need to be recognized by the system in order for it to provide an accurate representation of the treatment pattern. The physician may adjust the ultimate disposition of the beam on the patient's fundus by moving her head and/or the ophthalmic lens 19.

Figure 22:
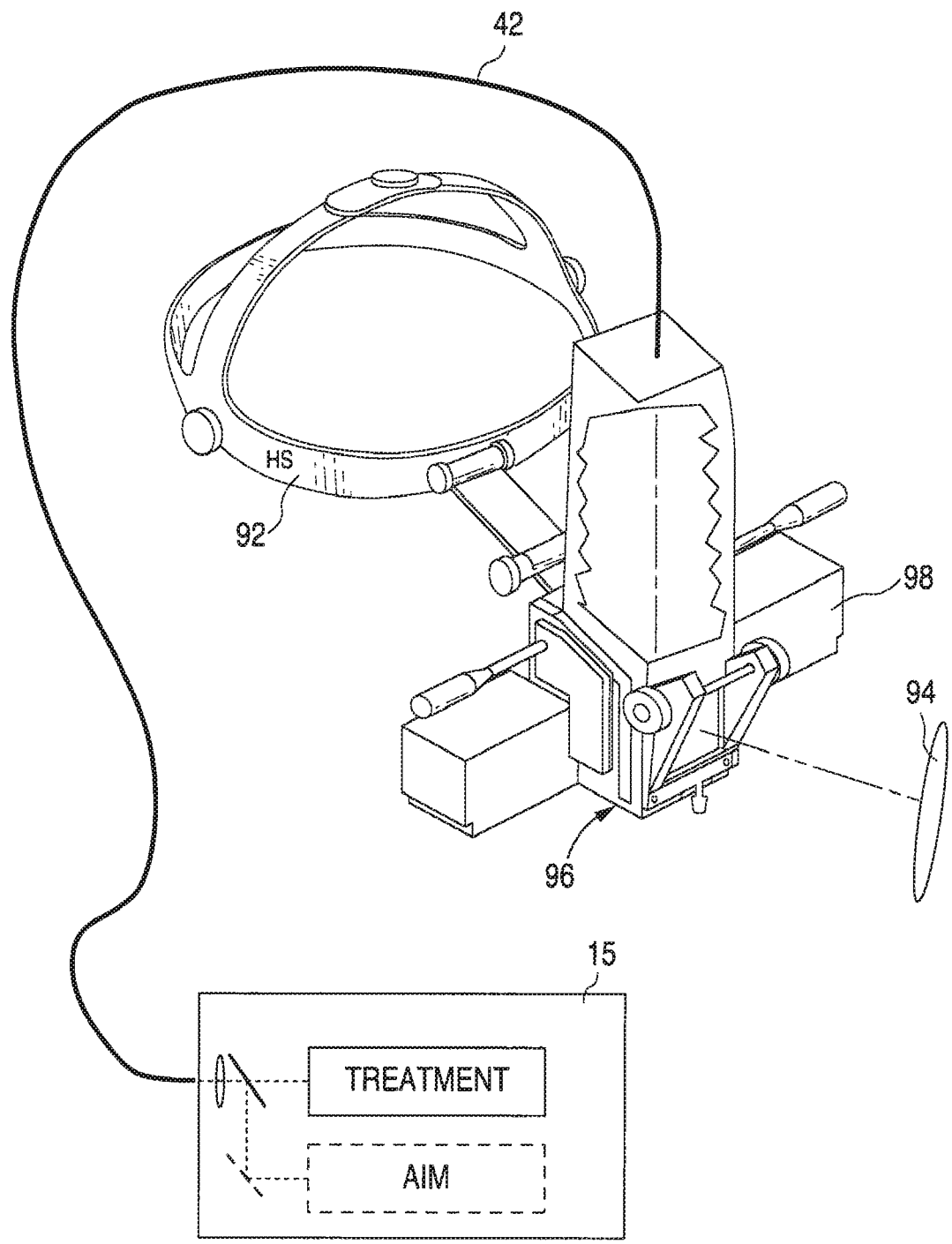

FIG. 22 is another schematic representation of the photomedical system 100 illustrating the LIO apparatus 16. Unlike the LIO apparatus 16 of FIG. 21, this LIO apparatus 16 shows an embodiment where the fiber unit 42 is a bundle of fibers capable of sequential and/or simultaneous spot delivery. The beam multiplier is not shown in FIG. 22 for simplicity of illustration, but the device may include or exclude the beam multiplier, as described above.

A "pattern," as defined herein is meant to include either the simultaneous or sequential delivery of a plurality of spots, such as those shown in FIGS. 4A-4I and 19. Likewise, "spots" are herein meant to describe either illumination with a static beam or a moving (scanned) beam. Each beam need not be round, but may be of any shape. For example, a non-circular cross-section fiber optic may be used in an imaging system to provide a beam of the same non-circular cross-section on the target tissue. Furthermore, any desired shapes may be created anamorphically or by scanning the beam, as described above. It should be noted that any of the treatment and/or aiming beam generation and control techniques, and/or any of the beam multiplying and/or scanning techniques, described herein can be implemented in combination with and/or incorporated as part of the head mounted LIO headset 92 shown in FIGS. 21 and 22.

Although the invention has been described with reference to the above examples, it will be understood that modifications and variations are encompassed within the spirit and scope of the invention. Accordingly, the invention is limited only by the following claims.

What is claimed is:

1. A photomedical system for treating eye tissue comprising:
   a treatment light source configured to generate a treatment light beam;
   a headset designed to be worn by a user, wherein the headset includes:
      an optical input configured to receive the treatment light beam;
      a beam multiplier configured to receive the treatment light beam and generate a plurality of treatment sub-beams by spatial separation of the treatment light beam, wherein the beam multiplier includes:
         a reflective diffraction element configured to convert the treatment light beam into the plurality of treatment sub-beams; and
         a dispersion compensating element positioned after the reflective diffraction element, wherein the dispersion compensating element is configured to receive a first treatment sub-beam of the plurality of treatment sub-beams;
      a lens positioned after the beam multiplier, wherein the lens is configured to receive the first treatment sub-beam directed from the dispersion compensating element and to receive a second treatment sub-beam of the plurality of treatment sub-beams from the reflective diffraction element;
      and a moveable mirror configured to receive the plurality of treatment sub beams first treatment sub-beam and the second treatment sub-beam from the lens and project the plurality of treatment sub-beams on the eye tissue in the form of a treatment pattern; and
   control electronics configured to cause the treatment light source, the beam multiplier, and the moveable mirror to automatically form the treatment pattern on the eye tissue.

2. The system of claim 1, wherein the beam multiplier is configured to receive the treatment light beam from the optical input.

3. The system of claim 2, wherein the headset further includes a zooming lens located between the optical input and the beam multiplier for adjusting a size of the treatment beam.

4. The system of claim 2, wherein the headset further includes a collimating lens located between the optical input and the beam multiplier.

5. The system of claim 1, wherein the treatment pattern comprises a plurality of discrete spots on the eye tissue.

6. The system of claim 5, wherein a number of discrete spots in the plurality of discrete spots is greater than a number of treatment sub-beams in the plurality of treatment sub-beams.

7. The system of claim 1, wherein the treatment pattern comprises a plurality of straight or curved lines on the eye tissue.

8. The system of claim 1, wherein the beam multiplier generates the plurality of treatment sub-beams by simultaneously dividing the treatment light beam into the plurality of treatment sub-beams.

9. The system of claim 1, wherein the beam multiplier includes an adaptive optic.

10. The system of claim 1, wherein the beam multiplier comprises an adjustable aperture configured to create the plurality of treatment sub-beams having a shape that is different from that of the treatment light beam.

11. The system of claim 1, further comprising an aiming light source configured to generate an aiming beam that is combined with the treatment light beam.

12. The system of claim 1, wherein the moveable mirror comprises an optical coating, and
   wherein the optical coating white balances the plurality of treatment sub-beams.

13. The system of claim 1, further comprising an ophthalmic lens configured to receive the plurality of treatment sub-beams and project the plurality of treatment sub-beams such that the plurality of treatment sub-beams pivot about a common point at an iris of the eye prior to being projected on the eye tissue, wherein the eye tissue is retina tissue of the eye.

* * * * *